(12) United States Patent
Stangl et al.

(10) Patent No.: US 10,234,322 B2
(45) Date of Patent: Mar. 19, 2019

(54) DEVICE FOR INTRODUCING A FREEZABLE LIQUID INTO THE EXHAUST GAS SYSTEM OF A MOTOR VEHICLE

(71) Applicant: Continental Automotive GmbH, Hannover (DE)

(72) Inventors: Ronny Stangl, Thalmassing (DE); Stephan Heinrich, Pfeffenhausen (DE); Denny Schaedlich, Neustadt (DE)

(73) Assignee: CONTINENTAL AUTOMOTIVE GMBH, Hanover (DE)

( * ) Notice: Subject to any disclaimer, the term of this patent is extended or adjusted under 35 U.S.C. 154(b) by 0 days.

(21) Appl. No.: 15/025,371

(22) PCT Filed: Sep. 25, 2014

(86) PCT No.: PCT/EP2014/070429
§ 371 (c)(1),
(2) Date: Mar. 28, 2016

(87) PCT Pub. No.: WO2015/044240
PCT Pub. Date: Apr. 2, 2015

(65) Prior Publication Data
US 2016/0238429 A1    Aug. 18, 2016

(30) Foreign Application Priority Data
Sep. 27, 2013 (DE) ........................ 10 2013 219 635

(51) Int. Cl.
*F01N 3/00* (2006.01)
*G01F 23/296* (2006.01)
(Continued)

(52) U.S. Cl.
CPC ........... *G01F 23/296* (2013.01); *F01N 3/206* (2013.01); *F01N 3/2896* (2013.01)

(58) Field of Classification Search
CPC ................. G01F 1/007; G01F 23/2968; F01N 2610/1406; G01N 2291/02836
(Continued)

(56) References Cited

U.S. PATENT DOCUMENTS

| 3,648,886 A | 3/1972 | Pringle | 220/723 |
| 4,322,226 A * | 3/1982 | Hudec | B01D 19/0078 95/266 |

(Continued)

FOREIGN PATENT DOCUMENTS

| DE | 2121823 A1 | 11/1971 | B60K 15/03 |
| DE | 10331566 A1 | 3/2004 | F02M 37/00 |

(Continued)

OTHER PUBLICATIONS

KR 101205234 B1 English Translation.*

(Continued)

*Primary Examiner* — Audrey K Bradley
*Assistant Examiner* — Anthony Ayala Delgado
(74) *Attorney, Agent, or Firm* — Slayden Grubert Beard PLLC

(57) ABSTRACT

The specification discloses a device for introducing a freezable liquid into the exhaust gas system of a motor vehicle. The device may include a tank for accommodating the freezable liquid, a sensor for determining the concentration and/or the filling level of the freezable liquid in the tank, and a dome-shaped ice protector. The sensor may be arranged at least partially in the tank, on the floor thereof. The dome-shaped ice protector may have rounded side faces which run together in the upward direction and have the purpose of protecting the part of the sensor which is located in the tank. The ice protector may be embodied in one piece with a floor plate of the sensor or with the tank floor and the dome of the ice protector has a completely open upper side.

14 Claims, 1 Drawing Sheet

(51) Int. Cl.
*F01N 3/20* (2006.01)
*F01N 3/28* (2006.01)

(58) Field of Classification Search
USPC .......................................................... 60/286
See application file for complete search history.

(56) References Cited

U.S. PATENT DOCUMENTS

| | | | |
|---|---|---|---|
| 4,964,090 A | 10/1990 | McCarthy | 367/162 |
| 6,993,967 B2 | 2/2006 | Forgue | 73/290 V |
| 7,117,738 B2 * | 10/2006 | Miyagawa | G01F 23/2962 |
| | | | 73/290 V |
| 9,556,774 B2 | 1/2017 | Hodgson et al. | |
| 2006/0288778 A1 | 12/2006 | Benner et al. | 73/313 |
| 2007/0084283 A1 | 4/2007 | Carlson et al. | 73/290 V |
| 2007/0157602 A1 * | 7/2007 | Gschwind | B60K 15/00 |
| | | | 60/274 |
| 2012/0118059 A1 * | 5/2012 | Reimer | F01N 3/2066 |
| | | | 73/290 V |
| 2014/0331650 A1 * | 11/2014 | Yang | F01N 11/00 |
| | | | 60/277 |
| 2014/0334983 A1 * | 11/2014 | Yang | F01N 11/00 |
| | | | 422/119 |
| 2014/0345377 A1 | 11/2014 | Jäger et al. | 73/290 V |

FOREIGN PATENT DOCUMENTS

| | | | |
|---|---|---|---|
| DE | 102011013687 A1 | 9/2012 | F01M 11/12 |
| DE | 102011089685 A1 | 6/2013 | G01F 23/296 |
| DE | 102012205640 A1 | 7/2013 | G01F 23/296 |
| EP | 1736743 A2 | 12/2006 | G01F 23/36 |
| JP | 3135735 A | 6/1991 | G01F 23/28 |
| JP | 2004101486 A | 4/2004 | B60K 15/03 |
| JP | 2004286528 A | 10/2004 | G01F 23/28 |
| JP | 2006144562 A | 6/2006 | B01D 53/94 |
| KR | 101205234 B1 * | 11/2012 | |
| WO | 2013/127804 A1 | 9/2013 | F01N 3/20 |
| WO | 2015/044240 A1 | 4/2015 | G01F 23/296 |

OTHER PUBLICATIONS

German Office Action, Application No. 102013219635.0, 6 pages, dated May 12, 2014.
International Search Report and Written Opinion, Application No. PCT/EP2014/070429, 18 pages, dated Jan. 7, 2015.
Chinese Office Action, Application No. 201480053156.4, 23 pages, dated Mar. 19, 2018.

* cited by examiner

DEVICE FOR INTRODUCING A FREEZABLE LIQUID INTO THE EXHAUST GAS SYSTEM OF A MOTOR VEHICLE

CROSS-REFERENCE TO RELATED APPLICATIONS

This application is a U.S. National Stage Application of International Application No. PCT/EP2014/070429 filed Sep. 25, 2014, which designates the United States of America, and claims priority to DE Application No. 10 2013 219 635.0 filed Sep. 27, 2013, the contents of which are hereby incorporated by reference in their entirety

TECHNICAL FIELD

The present disclosure relates to a device for introducing a freezable liquid into the exhaust gas system of a motor vehicle.

BACKGROUND

Devices for introducing a freezable liquid into the exhaust gas system of a motor vehicle are known. For example, a known device meters an aqueous urea solution for NOx reduction into the exhaust gas. The urea solutions used for this purpose are composed of distilled water and 32.5% urea. This solution freezes at −11° C. If the motor vehicle is switched off and the temperature of the liquid drops below −11° C., the solution in the tank freezes and the liquid may expand by up to approximately 11% in the frozen state.

It is also known in this context to monitor the content of the freezable liquid in the device, in particular in the tank, by means of a sensor. This sensor serves to determine the concentration and/or the filling level of the freezable liquid in the tank and is arranged at least partially in the tank, e.g., on the floor thereof. In this context, the sensor can have a separate floor which is connected to the floor of the tank, for example welded thereto, or the parts of the sensor can be arranged directly on the tank floor.

In particular, in this context an ultrasonic sensor may be used, said sensor arranged to determine the concentration and/or the filling level of the aqueous urea solution mentioned above. In this context, the concentration can be determined from the characteristic propagation time of the liquid through which the radiation passes (speed of sound in the medium). Typically, the corresponding ultrasonic transducer emits an acoustic wave which is reflected at one or more reflection surfaces arranged in the tank and is converted again at the transducer, serving here as a transmitter and as a receiver, as an electrical signal and used further. The distance between the transducer and the reflector (or the reflectors from one another) determines the accuracy of the measuring system.

If the liquid in the tank is frozen, the mass of ice which is formed can press on the part of the sensor located in the tank and, in particular, damage the references (reflectors) or all of that part of the sensor which is arranged in the tank. These forces can increase further in the case of a tank which has semi-thawed (lumps of ice) during travel as a result of acceleration and sloshing. In order to prevent this, the part of the sensor which is located in the tank may be provided with a dome-shaped ice protector which is attached to the floor of the sensor or of the tank. This usually semi-spherical arrangement allows the ice to slide over the protector and therefore not damage the part of the sensor which is arranged in the tank. The forces that can occur as a result of the ice which is caught in the protector are negligible.

An ultrasonic sensor in which the transmitter/receiver is arranged on the underside of the tank floor is commercially available. On the floor of the actual tank there is a plate (flange) on which the other parts of the sensor are arranged. This involves a mirror for deflecting in the horizontal direction the sound waves which are emitted vertically from the transmitter, two reflectors and a further mirror with which sound waves are deflected vertically upward. The ice protector of this sensor is attached to the floor plate of the sensor and has, above the second mirror, an opening so that the sound waves can be emitted upward through the opening into the tank and can be reflected back by the surface of the urea solution. In this embodiment, the ice protector is therefore essentially closed with the exception of the opening mentioned above.

However, with such a sensor and with such an ice protector, bubbles can form under the ice protector, specifically when refueling or as a result of outgassing of the gases (atmospheric oxygen) which are dissolved in the liquid (urea solution), which bubbles can collect the air under the dome or cap similarly to a diving bell and prevent measurement of the propagation time or temporarily "blind" the sensor until the bubbles become detached or dissolved. The time until the renewed readiness for measurement can range here between seconds and several hours. Since the ice protector is also a separate part, additional costs arise due to material costs, manufacturing costs, fabrication costs, logistical costs and assembly costs.

DE 103 31 566 A1 discloses a flow medium level sensor which has a housing component which is of hollow-cylindrical design and has the purpose of covering components of the sensor. Further measuring arrangements for determining a filling level and/or a concentration of a liquid are known from DE 10 2011 013 687 A1, DE 10 2012 205 640 A1 and DE 10 2011 089 685 A1.

SUMMARY OF THE INVENTION

The teachings of the present disclosure provide a device of the type described at the beginning which operates in a particularly functionally reliable fashion.

The ice protector which is embodied according to the invention is configured in a dome shape, e.g., has rounded side faces which run together in the upward direction. However, in contrast to the prior art, it has no essentially closed upper side, but instead a completely open upper side. In this way, the invention ensures that, on the one hand, the ice protector still has the necessary rigidity and the effect of conducting away forces but, on the other hand, prevents the formation of bubbles under the dome roof. The ice protector does not comprise a bubble trap which might influence the measurement of the sensor.

Since the rounded side walls of the dome of the ice protector are present, however, the ice which is formed in the tank slides over the protector and does not damage that part of the sensor which is arranged in the tank, in particular the mirrors and reflectors. The forces which are caused by the ice penetrating through the completely open upper side of the dome do not constitute any great risk here with respect to the part of the sensor which is arranged within the protector and are ultimately tolerated.

The ice protector may consist of only one piece connected to a floor plate of the sensor or to the tank floor. If the sensor has a separate floor plate which is arranged on the tank floor, the floor plate and the ice protector form one unit. If the sensor does not have a separate floor and if the corresponding part of the sensor is attached directly to the tank floor, the ice protector forms one unit with the tank floor. In both cases, an additional part which has to be attached to the sensor floor or tank floor is avoided. Therefore, various fabrication steps (combination of the ice protector with the respective floor, corresponding attachment, etc.) are dispensed with.

In some embodiments, the freezable liquid is, in particular, an aqueous urea solution. The sensor may comprise an ultrasonic sensor, wherein both the concentration and the filling level of the freezable liquid in the tank can be determined with the sensor.

In order to measure the concentration, the propagation time of the sound within the liquid may be measured with up to two reflectors which are arranged at different distances from the transmitter. During the measurement of the filling level, the propagation time up to the liquid surface at which the ultrasound is reflected is measured. Since the ice protector which is provided according to the invention has a completely open upper side, the ultrasonic wave can be deflected from its horizontal direction parallel to the floor of the sensor vertically upward through the upwardly open upper side of the ice protector.

It is important that the ice protector has a sufficient rigidity in order to apply a corresponding protective function for the part of the sensor which is arranged in the tank. In order to achieve this protective function, the dome of the ice protector may be reinforced by means of reinforcement fins. In this context, the dome has, in particular on its outer side, a structure made of longitudinally directed and/or transversely directed reinforcement fins. These intersecting reinforcement fins ensure a high degree of rigidity with low material expenditure.

Parts of the sensor, in particular of the ultrasonic sensor, can be suspended from the dome of the ice protector. In such embodiments, the corresponding parts of the sensor are therefore not attached to the sensor floor or tank floor but instead are supported by the upper region of the dome of the ice protector. In particular, this can involve the references (reflectors) and/or mirrors of the sensor being supported. Here, an embodiment in which a bar, from which the corresponding sensor parts, in particular the reference structure, are suspended, extends over the open upper side of the ice protector is preferred. This embodiment of the suspension provides particular advantages for the case in which bubbles form in the region of the floor of the sensor or tank, in particular at the reflectors or mirrors which are provided there. The corresponding parts can therefore be arranged at a distance from the floor by virtue of this type of attachment.

Formation of bubbles in the sound path of the ultrasonic sensor is therefore prevented by the completely open upper side of the ice protector, and on the other hand specific attachment of the sensor parts (reflectors, mirrors) is also made possible by suspension from the upper side of the dome.

BRIEF DESCRIPTION OF THE DRAWINGS

The invention will be explained in detail below on the basis of exemplary embodiments in conjunction with the drawing, in which.

DETAILED DESCRIPTION

Figure 1:
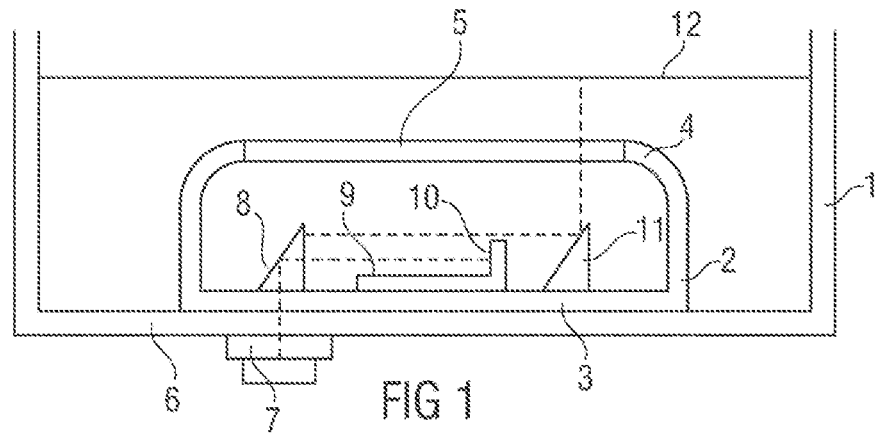
FIG. 1 shows a schematic vertical section through a liquid tank with a sensor for determining the concentration and the filling level of the liquid.

The tank 1 which is illustrated in a schematic vertical section in FIG. 1 is part of a device for introducing an aqueous urea solution into the exhaust gas system of a motor vehicle. The corresponding feed lines to the tank and discharge lines from the tank are not illustrated here. The surface of the aqueous urea solution which is located in the tank 1 is denoted by 12.

In order to measure the concentration and the filling level of the aqueous urea solution in the tank 1, an ultrasonic sensor is provided whose parts are illustrated schematically here. The ultrasonic sensor has an ultrasonic transducer 7 which acts as a transmitter and receiver and which is arranged on the underside of the floor 6 of the tank 1. In the interior of the tank 1 there is a unit which is composed of a floor plate 3 of the sensor and a dome-shaped ice protector 2 and which is embodied in one piece and fabricated from a suitable plastic. The upper side of the dome of the ice protector is completely open. The dome has here an approximately oval upper side opening 5. Further parts of the ultrasonic sensor, specifically a first sound mirror 8, a reference which has two reflectors 9, 10, and a second sound mirror 11, are located within the unit 2 which is composed of the ice protector and sensor floor 3. The ultrasonic wave which is output by the ultrasonic transducer 7 impinges on the first sound mirror 8 here and is deflected horizontally. Said ultrasonic wave impinges along its horizontal path on the two reflectors 9, 10 and is reflected thereby back to the receiver. A further part of the sound wave impinges on the second sound mirror 11 and is deflected upward by the latter. This part impinges on the surface 12 of the urea solution, is reflected thereby and passes back to the receiver along the same path. The concentration and the filling level of the urea solution can be determined by means of a corresponding propagation time measurement.

The ice protector which is embodied in a dome shape and which forms part of the unit 2 has a rounded side wall 4, with the result that ice which is formed when the urea solution freezes in the tank 1 is conducted away upward over the parts of the ultrasonic sensor and does not damage these parts. The oval upper side opening 5 of the ice protector prevents bubbles which have a disadvantageous effect on the ultrasonic measurement from collecting within the protector.

Figure 2:
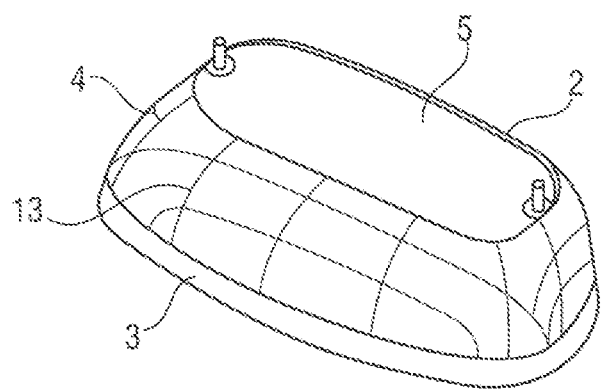
FIG. 2 shows a spatial illustration of a unit which is composed of a sensor floor and an ice protector.

FIG. 2 shows the single-piece unit which is formed from the ice protector and the floor plate 3, in a schematic view. The dome of the ice protector is open in the upward direction and has there an approximately oval upper side opening 5. The side wall of the ice protector is correspondingly rounded, with the result that ice which is formed is deflected upward and does not impinge on the sensor parts.

Figure 3:
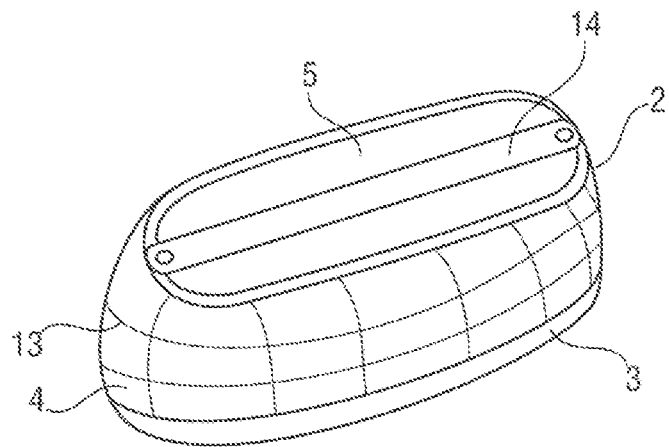
FIG. 3 shows a further embodiment of a unit which is composed of a sensor floor and an ice protector, with a device for suspending the sensor reference.

FIG. 3 shows a schematic spatial view of a further embodiment of a single-piece unit 2 which is composed of a floor plate 3 and ice protector. This unit 2 is provided on its upper side with a bar 14 which spans the oval upper side opening 5 and from which the reference which is composed of the reflectors 9, 10 is suspended (not shown). As a result, the reference is supported at a distance from the floor 3, with the result that bubbles which have collected there do not disrupt the measurement.

In order to reinforce the side wall 4 of the unit 2, in both embodiments of FIGS. 2 and 3 a structure composed of longitudinally directed and transversely directed reinforcement fins 13 is provided on the outer side of said side wall 4.

What is claimed is:

1. A device for introducing a freezable liquid into the exhaust gas system of a motor vehicle, the device comprising:
    a tank for accommodating the freezable liquid,
    a dome-shaped ice protector with rounded side walls without perforations that block a lateral flow of the freezable liquid into an interior of the ice protector, and an open upper side allowing a vertical flow of the freezable liquid into the interior of the ice protector, wherein in a vertical cross-sectional plane extending through the dome-shaped ice protector, the rounded side walls are curved such that upper portions of the rounded side walls extend laterally toward a center of the open upper side of the ice protector, and
    a sensor for determining the concentration and/or the filling level of the freezable liquid in the tank, which sensor is mounted to the ice protector or to a tank floor so that no part of the sensor extends through the open upper side of the ice protector,
    wherein the ice protector is embodied in one piece with a floor plate of the sensor or with the tank floor.

2. The device as claimed in claim 1, wherein the freezable liquid is an aqueous urea solution.

3. The device as claimed in claim 1, wherein the sensor is an ultrasonic sensor.

4. The device as claimed in claim 1, wherein the open upper side of the ice protector has an approximately oval shape.

5. The device as claimed in claim 1, wherein parts of the sensor are suspended from the rounded side walls of the ice protector.

6. The device as claimed in claim 1, further comprising a bar extended across the open upper side of the ice protector, wherein parts of the sensor are suspended from the bar.

7. An exhaust gas system for a motor vehicle, system comprising:
    a conduit channeling exhaust gas from at least one combustion chamber,
    a controller for metering a freezable liquid into the conduit for adjusting an NOx concentration in the exhaust gas,
    a tank for accommodating the freezable liquid,
    an ice protector having a housing with rounded side walls without perforations which run together in the upward direction to define an interior chamber of the ice protector, the ice protector housing blocking a lateral flow of the freezable liquid into the interior chamber of the ice protector, the rounded side walls of the ice protector housing curving inwardly and terminating at an upper edge that defines an open upper side allowing a vertical flow of the freezable liquid into the interior chamber of the ice protector, wherein due to the inward curvature of the rounded side walls, a lateral area of the interior chamber decreases along a vertically upward direction toward the upper open side, and
    a sensor for determining the concentration and/or the filling level of the freezable liquid in the tank, which sensor is mounted to the ice protector or to a tank floor so that no part of the sensor extends through the open upper side.

8. The system as claimed in claim 7, wherein the freezable liquid is an aqueous urea solution.

9. The system as claimed in claim 7, wherein the sensor is an ultrasonic sensor.

10. The system as claimed in claim 7, wherein the open upper side of the ice protector has an approximately oval shape.

11. The system as claimed in claim 7, wherein parts of the sensor are suspended from the rounded side walls of the ice protector housing.

12. The device as claimed in claim 11, further comprising a bar extending across the open upper side of the ice protector, wherein parts of the sensor are suspended from the bar.

13. The system as claimed in claim 7, wherein the ice protector is embodied in one piece with a floor plate of the sensor or with the tank floor.

14. A device for introducing a freezable liquid into the exhaust gas system of a motor vehicle, the device comprising:
    a tank for accommodating the freezable liquid,
    an ice protector with rounded side faces without perforations which run together in the upward direction and block a lateral flow of the freezable liquid into an interior of the ice protector, and an open upper side allowing a vertical flow of the freezable liquid into the interior of the ice protector, the open upper side having an approximately oval shape, and
    a sensor for determining the concentration and/or the filling level of the freezable liquid in the tank, which sensor is mounted to the ice protector or to a tank floor so that no part of the sensor extends through the open upper side of the ice protector,
    wherein the ice protector is embodied in one piece with a floor plate of the sensor or with the tank floor.

* * * * *